(12) United States Patent
Omarsson et al.

(10) Patent No.: US 10,292,454 B2
(45) Date of Patent: May 21, 2019

(54) LATERAL WEDGE

(71) Applicant: Ossur Iceland ehf, Reykjavik (IS)

(72) Inventors: Bjorn Omarsson, Reykjavik (IS); Halldor Albertsson, Aalborg Ost (DK); Thorleifur Stefansson, Akureyri (IS); Larus Gunnsteinsson, Reykjavik (IS); Arni Thor Ingimundarson, Gardabaer (IS)

(73) Assignee: Ossur Iceland, ehf, Reykjavik (IS)

( * ) Notice: Subject to any disclaimer, the term of this patent is extended or adjusted under 35 U.S.C. 154(b) by 458 days.

(21) Appl. No.: 15/008,789

(22) Filed: Jan. 28, 2016

(65) Prior Publication Data

US 2016/0220375 A1 Aug. 4, 2016

Related U.S. Application Data

(60) Provisional application No. 62/109,446, filed on Jan. 29, 2015.

(51) Int. Cl.
- *A43B 17/02* (2006.01)
- *A61F 5/14* (2006.01)
- *A61F 5/01* (2006.01)

(52) U.S. Cl.
CPC ............ *A43B 17/023* (2013.01); *A43B 17/02* (2013.01); *A61F 5/0127* (2013.01); *A61F 5/14* (2013.01);
(Continued)

(58) Field of Classification Search
CPC ..... A43B 17/02; A43B 17/023; A61F 5/0106; A61F 5/0123; A61F 5/0127; A61F 5/14
(Continued)

(56) References Cited

U.S. PATENT DOCUMENTS

| 1,187,578 A | 6/1916 | Watrous |
| 1,408,712 A | 3/1922 | Patten |

(Continued)

FOREIGN PATENT DOCUMENTS

| DE | 883046 C | 7/1953 |
| GB | 2451739 A | 2/2009 |
| JP | 2001017202 A | 1/2001 |

OTHER PUBLICATIONS

"Treatment of Osteoarthritis of the Knee (Non-Arthroplasty)", Clinical Practice Guideline, American Academy of Orthopaedic Surgeons, Dec. 6, 2008, 265 pages.
(Continued)

*Primary Examiner* — Keri J Nelson
(74) *Attorney, Agent, or Firm* — Workman Nydegger

(57) ABSTRACT

An orthopedic device includes a lateral wedge positionable under a foot of a user. The lateral wedge has posterior and anterior ends, and upper and lower surfaces. First and second sides extend between the upper and lower surfaces. A thickness is defined between the upper and lower surfaces that tapers from the first side toward the second side such that the lateral wedge provides a lift under the foot to unload pressure from an affected compartment of the knee by supporting a one side of the foot in an elevated position relative to the other. At least one trim line extends in a direction between the posterior and anterior ends. The lateral wedge is trimmable along the at least one trim line to vary or control the amount of lift provided by varying the thickness of the lateral wedge along the first side relative to the second side.

19 Claims, 8 Drawing Sheets

(52) U.S. Cl.
CPC ........... *A61F 5/0106* (2013.01); *A61F 5/0123* (2013.01); *A61F 2230/0086* (2013.01)

(58) Field of Classification Search
USPC .......................... 36/43, 44, 144; 602/23, 26
See application file for complete search history.

(56) References Cited

U.S. PATENT DOCUMENTS

| | | | |
|---|---|---|---|
| 2,097,959 A | | 11/1937 | Whitman |
| 4,387,516 A | * | 6/1983 | Laux ................ A43B 3/0078 33/3 R |
| 4,841,648 A | | 6/1989 | Shaffer et al. |
| 4,862,605 A | | 9/1989 | Gardner et al. |
| 5,092,347 A | | 3/1992 | Shaffer et al. |
| 5,138,774 A | | 8/1992 | Sarkozi |
| 5,345,701 A | | 9/1994 | Smith |
| 5,579,591 A | | 12/1996 | Kousaka et al. |
| 6,205,685 B1 | * | 3/2001 | Kellerman ........... A43B 1/0072 36/160 |
| 6,604,301 B1 | | 8/2003 | Manoli, II et al. |
| 6,725,578 B2 | | 4/2004 | Kerrigan |
| 6,742,289 B2 | | 6/2004 | Celmo |
| 7,198,610 B2 | | 4/2007 | Ingimundarson et al. |
| 7,201,728 B2 | * | 4/2007 | Sterling ................ A61F 5/0123 602/16 |
| 7,210,250 B2 | | 5/2007 | Gallegos |
| 7,373,740 B2 | | 5/2008 | Lo |
| 7,475,498 B2 | | 1/2009 | Litchfield et al. |
| 7,484,318 B2 | | 2/2009 | Finkelstein |
| 7,484,319 B2 | | 2/2009 | Cheskin et al. |
| 7,849,612 B2 | | 12/2010 | Epstein |
| 8,007,456 B2 | | 8/2011 | Stano |
| 8,122,550 B2 | | 2/2012 | Johnson |
| 8,371,047 B2 | | 2/2013 | Johnson |
| 8,523,194 B2 | | 9/2013 | Smirman |
| 2001/0047146 A1 | | 11/2001 | Toda |
| 2003/0005599 A1 | | 1/2003 | Panaccione |
| 2006/0053664 A1 | | 3/2006 | Tager |
| 2006/0135904 A1 | | 6/2006 | Ingimundarson et al. |
| 2008/0034618 A1 | | 2/2008 | Lin |
| 2009/0031583 A1 | * | 2/2009 | Avent ................ A43B 7/144 36/88 |
| 2010/0018074 A1 | | 1/2010 | Greene |
| 2010/0154252 A1 | | 6/2010 | Avent et al. |
| 2010/0192418 A1 | | 8/2010 | Johnson |
| 2011/0131841 A1 | | 6/2011 | Foster |
| 2012/0055045 A1 | | 3/2012 | Wang |
| 2012/0144696 A1 | | 6/2012 | Johnson |
| 2014/0371648 A1 | | 12/2014 | Deheer et al. |
| 2015/0196086 A1 | | 7/2015 | Riddle |

OTHER PUBLICATIONS

International Search Report from corresponding PCT Application No. PCT/US2016/015293, dated May 13, 2016.

\* cited by examiner

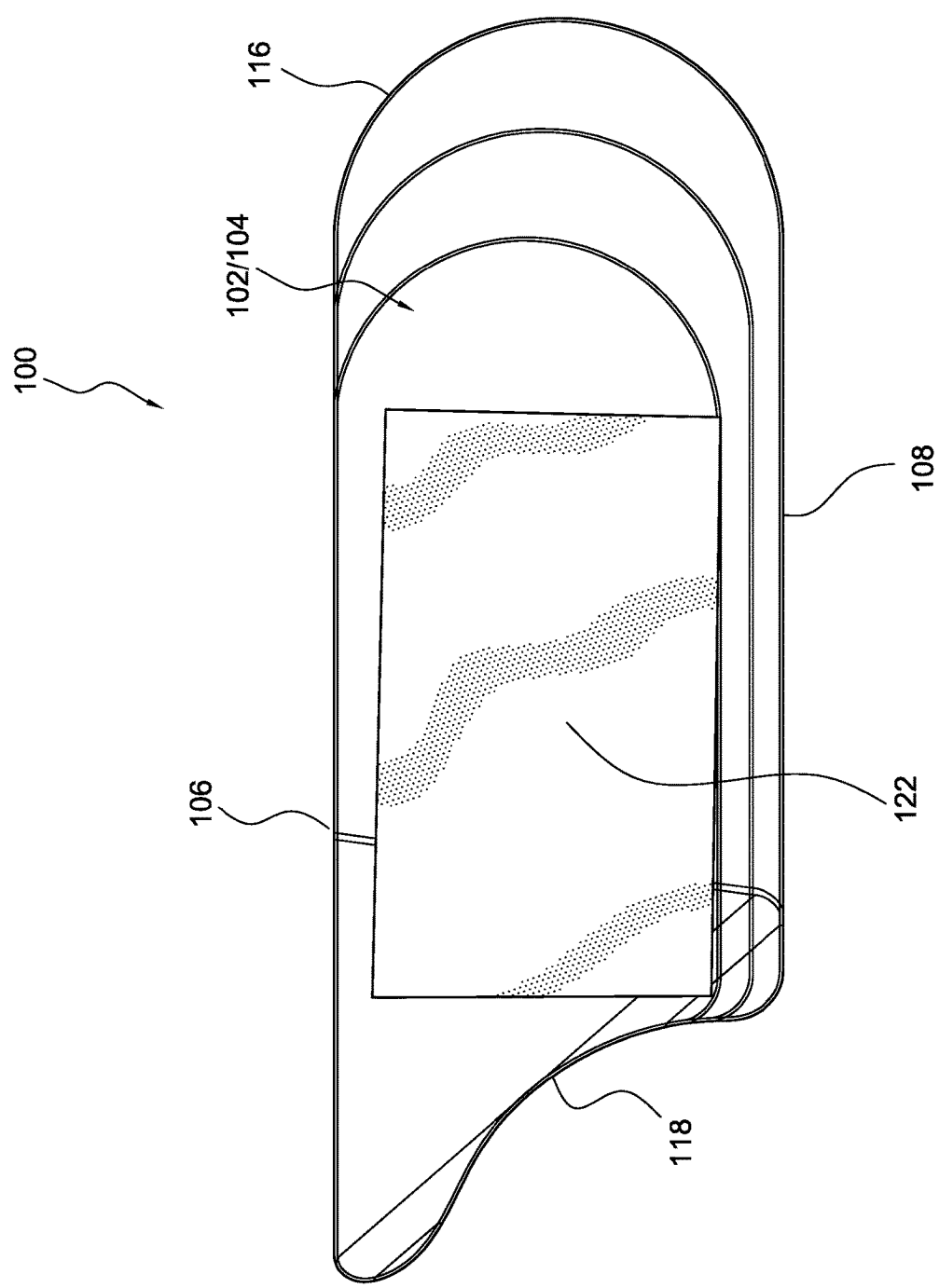

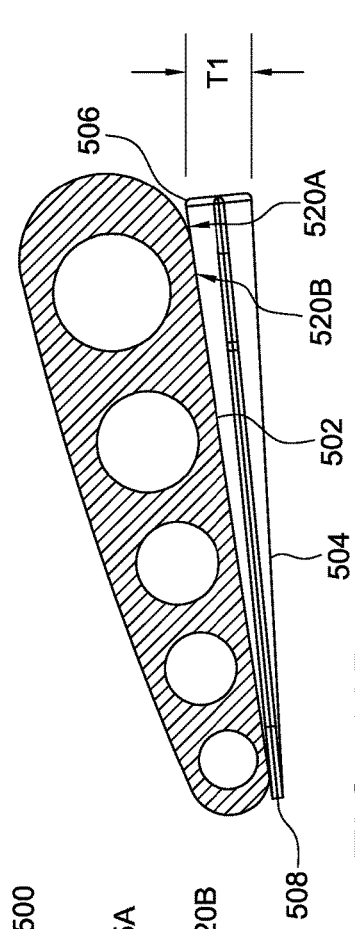
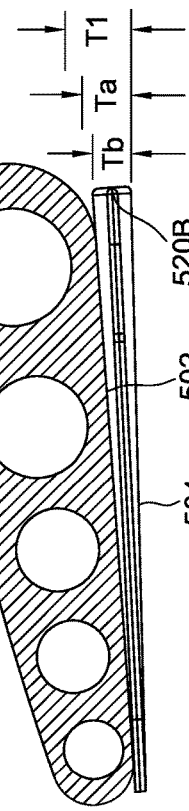
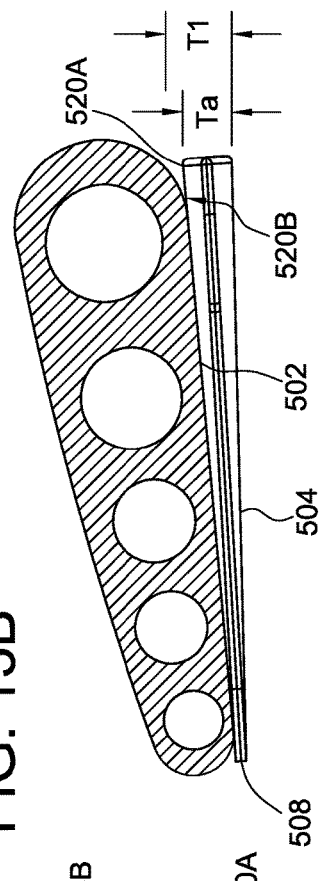
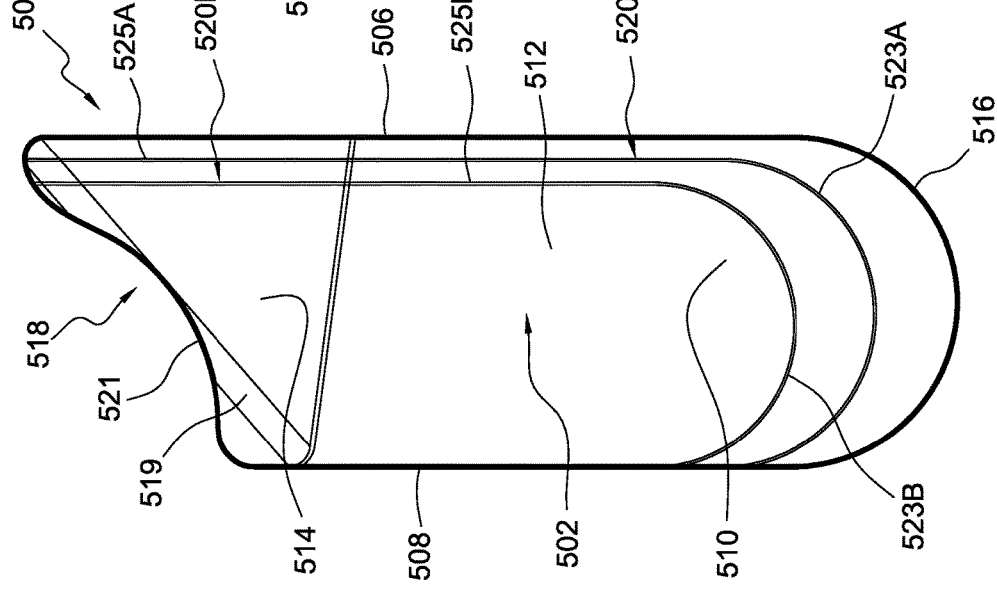
FIG. 13A
FIG. 13B
FIG. 13C
FIG. 13D

LATERAL WEDGE

TECHNICAL FIELD

The disclosure relates to a lateral wedge for use in the treatment of joint diseases and/or structural biomechanical abnormalities.

BACKGROUND

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or simply due to aging of the knee.

A major problem resulting from osteoarthritis of the knee is that the smooth cartilage lining the inside of the knee wears away. This leads to a narrowing of the joint space with the development of cysts and erosions in the bone ends. Because of the narrowing of the joint, bone comes directly in contact with bone, and an uneven distribution of pressure develops across the knee which may result in the formation of bone spurs around the joint. All of these changes ultimately lead to increasing pain and stiffness of the joint.

While there are no cures to osteoarthritis, there are many treatments. Individuals who have a diagnosis of isolated medial or lateral compartmental osteoarthritis of the knee are confronted with a variety of treatment options such as medications, surgery, and nonsurgical interventions.

One type of nonsurgical intervention is knee bracing. Knee bracing is useful to provide compartmental pain relief by reducing the load on the affected compartment through applying an opposing external valgus or varus moment about the knee joint. Unloading knee braces have been shown to significantly reduce osteoarthritis knee pain while improving knee function. Many users however find these braces uncomfortable, bulky, and/or limited in their ability to unload the affected compartment of the knee.

SUMMARY

The disclosure describes various embodiments of a lateral wedge providing a construction and design that facilitates more comfortable and effective support of a user's foot during the treatment of joint disease (e.g., osteoarthritis) of the knee and/or structural biomechanical abnormalities of the user's foot and/or ankle.

The embodiments described can include a lateral wedge having posterior and anterior ends, and upper and lower surfaces extending between the posterior and anterior ends. A first side extends between the upper and lower surfaces, and a second side is opposed the first side. A ramped surface is formed in the upper surface and extends diagonally between the first and second sides. A thickness is defined between the upper and lower surfaces. The thickness tapers from the first side toward the second side, which, in turn, causes the lateral wedge to provide a lift under the foot by supporting a lateral side of the foot or a medial side of the foot in an elevated position relative to the other.

The lift provided by the lateral wedge changes the angle and position of the foot-ground interface. This can beneficially unload a compartment of the knee to reduce bone on bone contact, which, in turn, can help relieve pain and stiffness caused by, for example, medial compartmental OA of the knee. It should be appreciated that the level of stress or load relief provided by the lateral wedge can depend in part on the amount of lift provided by the lateral wedge.

Embodiments of the lateral wedge may include at least one trim line extending in a direction between the posterior and anterior ends that is arranged to vary or control the amount of lift provided by the lateral wedge. In order to vary or adjust the amount of lift, the thickness of the first side relative to the second side can be controlled by trimming the lateral wedge along the at least one trim line. The at least one trim line can extend between the upper and lower surfaces, between the first and second sides, between the posterior and anterior ends, or combinations thereof. Further, the degree of adjustment or control available can be based on a desired treatment protocol, needs of a patient, and/or other requirements. This facilitates more comfortable and effective support of a user's foot during treatment of joint disease and/or structural biomechanical abnormalities.

According to a variation, the upper and lower surfaces of the lateral wedge can have a same contour between the posterior and anterior ends. This beneficially allows the lateral wedge to be used on either right or left feet, with any appropriate reconfiguration of components that is deemed necessary for the proper fit and function of the lateral wedge for the purpose of treatment, repair, and/or rehabilitation of the knee of either the left or right leg. Further, the lateral wedge may provide a lift to the medial or lateral side foot depending on whether the lateral or medial side of the knee is affected.

According to a variation, embodiments of the lateral wedge can be used in combination with an unloading knee brace. Unloading knee braces are specifically designed to apply a corrective torque (moment or force) to a varus or valgus deformity associated with compartmental OA.

Using the lateral wedge with the unloading knee brace can provide a more effective mechanism for relieving compartmental OA. For instance, by unloading the affected compartment of the knee with both the lateral wedge and an unloading knee brace, the unloading from the lateral wedge can be substituted for a portion of the unloading normally provided by the unloading knee brace. This can advantageously lower the level of unloading required from the unloading knee brace, allowing the knee brace to be made smaller and/or simpler than in the prior art. This can result in unloading knee braces that are less bulky, lighter-weight, and more comfortable to wear.

Unloading the affected compartment of the knee with both the lateral wedge and the unloading knee brace can also augment unloading of the knee. By unloading the affected compartment of the knee with both the lateral wedge and the unloading knee brace, the affected area of the knee can be unloaded to a level above the functional capacity of the knee brace alone. This advantageously provides greater pain reduction and increased mobility levels in the knee, improving management of the symptoms of compartmental OA of the knee.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth hereinafter.

BRIEF DESCRIPTION OF THE DRAWINGS

To further clarify the above and other advantages and features of the present disclosure, a more particular description of the disclosure will be rendered by reference to specific embodiments illustrated in the drawings. It is appreciated that these drawings depict only typical embodiments of the disclosure and are not to be considered limiting of scope, and are not necessarily drawn to scale. The disclosure will be described and explained with additional specificity and detail through the use of the accompanying drawings.

FIG. 9 is a bottom view of the lateral wedge according to an embodiment.

FIG. 13A is a top view of a lateral wedge according to another embodiment.

FIG. 13B is a front view of the lateral wedge of FIG. 13A.

FIG. 13C is a front view of the lateral wedge of FIG. 13A trimmed along a first trim line.

FIG. 13D is a front view of the lateral wedge of FIG. 13A trimmed along a second trim line.

DETAILED DESCRIPTION

Figure 1:
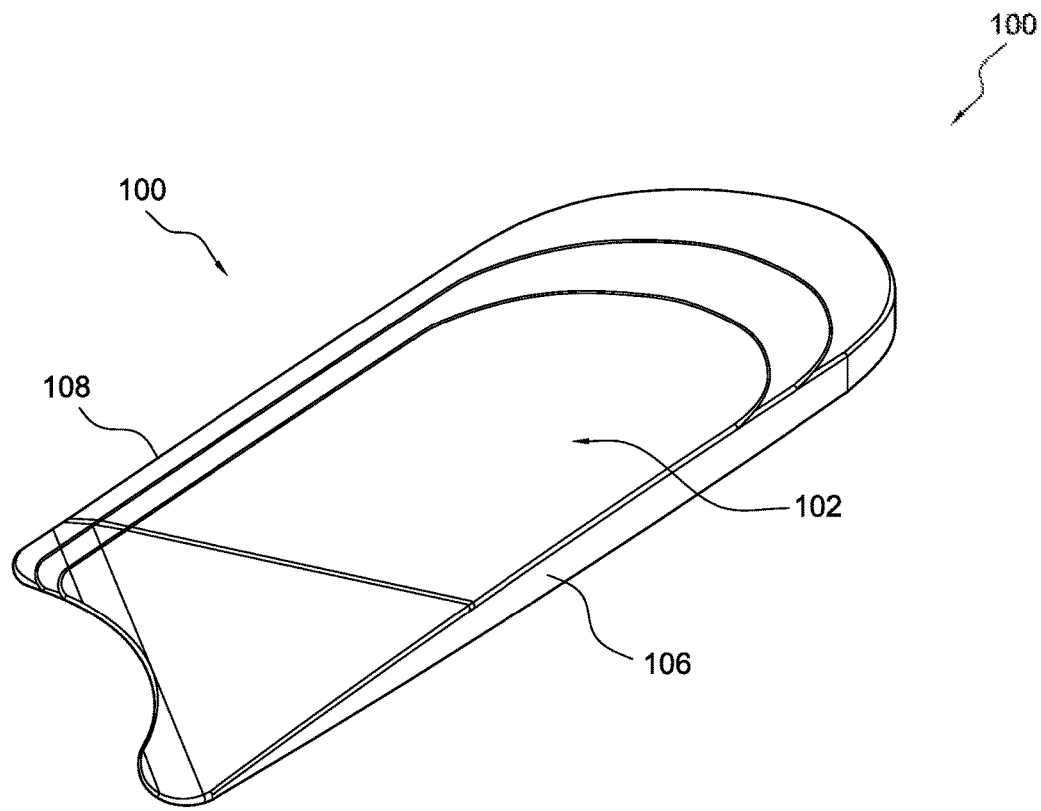
FIG. 1 is an isometric view of a lateral wedge according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that, unless a term is expressly defined in this disclosure to possess a described meaning, there is no intent to limit the meaning of such term, either expressly or indirectly, beyond its plain or ordinary meaning.

Exemplary embodiments of a lateral wedge can be used as a treatment option for isolated compartmental osteoarthritis (OA) of the knee in parallel with an unloading knee brace or alone to unload a force or pressure from an affected compartment of the knee. Features that are provided on one side of the lateral wedge can easily be provided on the other side of the wedge. In this manner, it is intended that the exemplary embodiments of the lateral wedge described herein may be used on either right or left feet, with any appropriate reconfiguration of components that is deemed necessary for the proper fit and function of the lateral wedge for the purpose of treatment, repair, and rehabilitation of the knee of either the left or right leg. Further, the lateral wedge may be configured to provide a lift to the medial or lateral side of the foot depending on whether the lateral or medial side of the knee is affected.

The exemplary embodiments of the lateral wedge can be implemented in various orthopedic devices, including, but not limited to, configurations of ankle foot orthosis, orthopedic shoes, or post-surgical shoes. The lateral wedge can be implemented in footwear, including, but not limited to, configurations of shoes, boots, slippers, or sandals. The exemplary embodiments of the disclosure are adapted for treatment, repair, and/or rehabilitation of the knee of human beings, and may be dimensioned to accommodate different types, shapes and sizes of human joints and appendages.

For further ease of understanding the exemplary embodiments as disclosed herein, a description of a few terms is necessary. As used herein, the term "dorsal" has its ordinary meaning and refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," and "resilient" may be used herein to distinguish characteristics of portions of certain features of the orthopedic device. The term "rigid" is intended to denote that an element of the device is generally devoid of flexibility. Within the context of support members or shells that are "rigid," it is intended to indicate that they do not lose their overall shape when force is applied, and in fact they may break if bent with sufficient force. On the other hand, the term "flexible" is intended to denote that features are capable of repeated bending such that the features may be bent into retained shapes or the features do not retain a general shape, but continuously deform when force is applied. The term "resilient" is used to qualify such flexible features as generally returning to an initial general shape without permanent deformation. As for the term "semi-rigid," this term is used to denote properties of members that provide support and are free-standing; however such support members or shells may have some degree of flexibility or resiliency.

Figure 2:
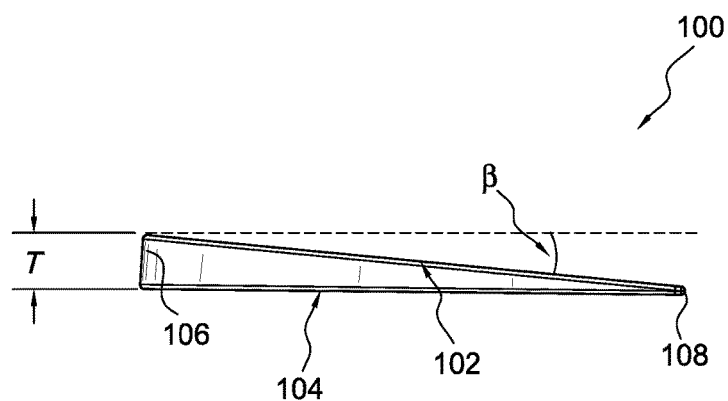
FIG. 2 is a back view of the lateral wedge shown in FIG. 1.

Referring to FIGS. 1 and 2, a first exemplary embodiment of an orthopedic system 3 includes a lateral wedge 100 having an upper surface 102, a lower surface 104, and opposite first and second or lateral and medial sides 106, 108. A portion of the foot can rest on the upper surface 102 and the lower surface 104 can interface with a support surface. The support surface can comprise an insole, a liner, or the interior bottom of typical footwear, orthopedic devices, post-surgical shoes, or other suitable support surface. During use, the lateral side 106 of the lateral wedge 100 can be positioned along the lateral side of the foot and the medial side 108 of the lateral wedge 100 can be positioned along the medial side of the foot. Optionally, the lateral wedge 100 can include radii on one or more of the bottom and/or upper edges. This can beneficially help increase the comfort of the lateral wedge 100.

As seen in FIG. 2, the lateral wedge 100 includes a thickness T defined between the upper and lower surface 102, 104. The lateral wedge 100 includes a vertical component such that when the lateral wedge 100 is positioned underneath the foot, the lateral side of the foot is supported in an elevated position relative to the remainder of the foot, providing a lateral lift under the foot. The thickness T tapers from the lateral side 106 of the lateral wedge 100 toward the medial side 108 so that the upper surface 102 descends or generally slopes downward from the lateral side 106 toward the medial side 108. In the illustrated embodiment, the upper surface 102 slopes downward linearly, such that the lateral wedge 100 is generally wedge-shaped. In other embodiments, the upper surface 102 can slope downward in a concave, convex, stepped, or in any other suitable fashion.

The upper surface 102 extends at a downward angle β relative to horizontal between the lateral side 106 and the medial side 108. The downward angle β and the thickness T of the lateral side 106 relative to the medial side 108 beneficially act to provide the lateral lift under the foot. By controlling the angle β and/or thickness T, the amount of lateral lift can be controlled. For instance, increasing the angle β can increase the thickness T of the lateral side 106 relative to the medial side 108, which, in turn, can increase the amount of lateral lift. Conversely, decreasing the angle β can decrease the thickness T of the lateral side 106 relative to the medial side 108, which, in turn, can decrease the amount of lateral lift.

The angle β can be between about 0.5 degrees and about 20 degrees, about 1 degree and about 16 degrees, about 2 degrees and about 12 degrees (e.g., about 2.5 degrees), between about 4 degrees and about 10 degrees, or between about 5 degrees and 8 degrees. In other embodiments, the angle β can be more or less. The angle β can be selected based on one or more anatomical features of the user. The angle β can be constant or variable.

The thickness T of the lateral side 106 can be between about 2 times and about 12 times, about 3 times and about 10 times, about 4 times and about 8 times, or about 5 times and about 7 times greater than the thickness of the medial side 108. The thickness T of the lateral side can be greater than about 2 times, about 4 times, about 6 times, about 8 times, or about 10 times the thickness T of the medial side 108. In other embodiments, the thickness T of the lateral side 106 can be more or less relative to the medial side 108.

Figure 3:
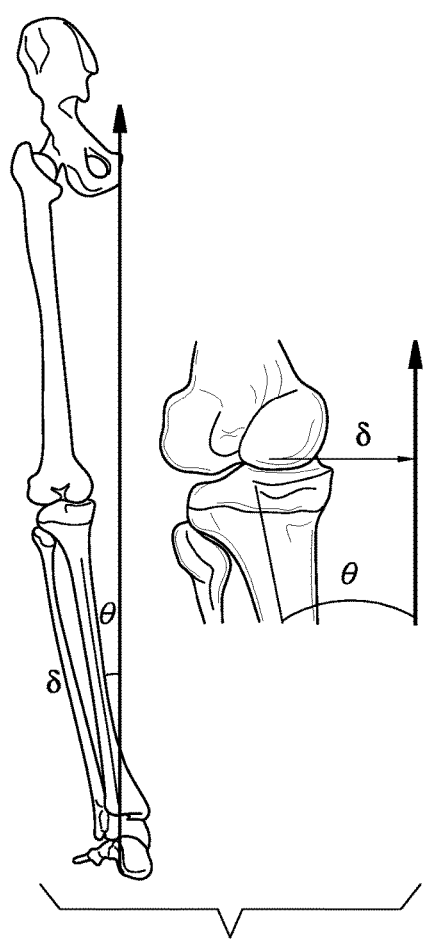
FIG. 3 is a schematic view of forces applied on a leg without a lateral wedge.
Figure 4:
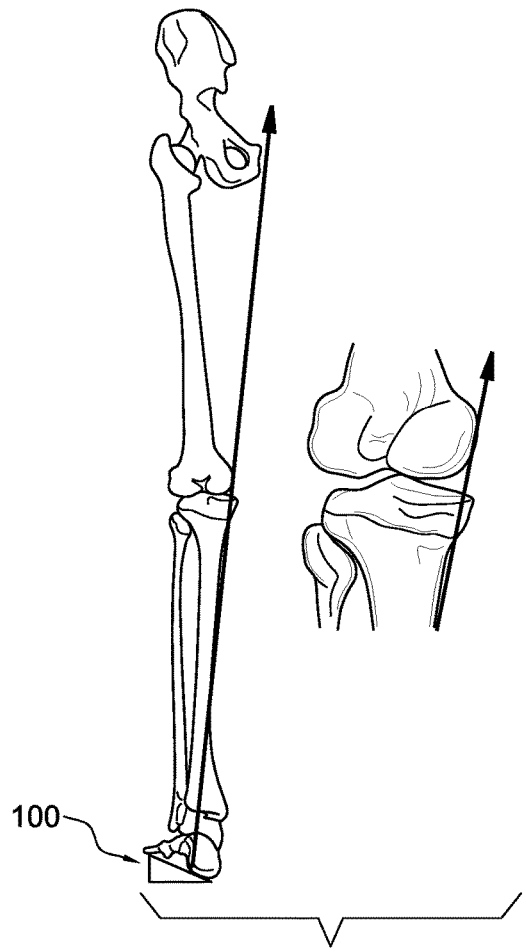
FIG. 4 is a schematic view of forces applied on the leg with a lateral wedge according to an embodiment.

Referring now to FIGS. 3 and 4, the lateral lift provided by the lateral wedge 100 can advantageously unload the medial compartment of the knee, which, in turn, can help relieve pain and stiffness caused by medial compartmental OA of the knee. The term "gait" is generally defined as the coordinated sequence of the various biomechanical movements of the lower limbs of a person undergoing locomotion. Walking is a typical gait cycle and is divided into two phases. The first phase is the stance phase, which comprises the weight bearing portion of each gait cycle and is initiated by heel contact or heel-strike and ends with toe-off of the same foot. The second phase is the swing phase, which is initiated with toe-off and ends with heel-strike.

When walking, a ground reaction force ("GRF") is generated that places each of the foot, ankle, and leg under some level of stress. A GRF vector originates at the foot-ground interface during the stance phase of gait as seen in FIG. 3. The GRF vector includes a magnitude (e.g., represented by the height of the vector) and direction (e.g., represented by angle θ). An external moment is associated with the GRF and a moment arm, defined as the distance δ from the knee joint axis to the GRF. As the knee becomes more varus, the moment arm δ increases, which, in turn, increases the magnitude of the external moment and stress at the medial knee compartment.

As seen in FIG. 4, the lateral wedge 100 can be situated under the foot such that the lateral wedge 100 provides the lateral lift to the foot. This lateral lift changes the angle and position of the foot-ground interface, reducing the angle θ or shifting the direction of the GRF vector more laterally toward the center of the knee. This beneficially decreases the moment arm δ, which, in turn, reduces the external moment and load at the medial knee compartment. As a result, the lateral wedge 100 can reduce bone on bone contact, relieving pain and stiffness in the medial knee compartment.

It will be appreciated that while the lateral wedge 100 is described unloading the medial compartment of the knee, in other embodiments, the lateral wedge 100 can be configured to unload the lateral compartment of the knee. For instance, the lateral wedge 100 can support the medial side of the foot in an elevated position relative to the remainder of the foot. As such, the lateral wedge 100 can unload the lateral compartment of the knee, treating isolated lateral compartmental OA of the knee.

It should be appreciated that the level of stress or load relief provided by the lateral wedge 100 can depend in part on the amount of lateral lift provided by the lateral wedge 100. For instance, increasing the angle β can increase the amount of lateral lift provided by the lateral wedge 100, which, in turn, can increase the unloading of the affected compartment provided by the lateral wedge 100. In an embodiment, the level of stress relief provided by the lateral wedge 100 can be selected based on a target stress relief. The target stress relief can be based on one or more anatomical features of the user. The target stress relief can be based on a treatment regimen. The level of stress relief provided by the lateral wedge 100 can be adjustable.

Figure 5:
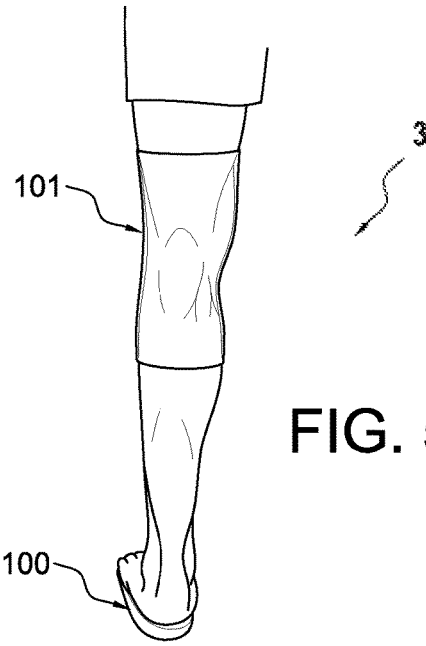
FIG. 5 is a schematic view of a leg with a lateral wedge and knee brace according to an embodiment.

Optionally, the orthopedic system 3 includes the lateral wedge 100 and an unloading knee brace 101 as seen in FIG. 5. For instance, the lateral wedge 100 can be used as a treatment option for isolated compartmental OA of the knee in parallel use with the unloading knee brace 101. Unloading knee braces are specifically designed to apply a corrective torque (moment or force) to a varus or valgus deformity associated with compartmental OA. Typically, they are designed to dynamically off-load the affected compartment of the knee via angulation of hinge components and/or a three-point bending system via a force strap that spirals around the knee and applies a force to a prescribed aspect of the knee. Such mechanisms can generate undesirable rotational forces in the knee brace, which, in turn, can limit the unloading provided by the knee brace. It will be appreciated that the unloading knee brace 101 may be any type of knee brace. For instance, the unloading knee brace 101 may be a knee brace as described in U.S. Pat. No. 7,198,610, incorporated by reference and belonging to the assignee of this disclosure.

Using the lateral wedge 100 with an unloading knee brace 101 can provide a more effective mechanism for relieving compartmental OA. For instance, by unloading the affected compartment of the knee with both the lateral wedge 100 and an unloading knee brace 101, the unloading from the lateral wedge 100 can be substituted for a portion of the unloading normally provided by the unloading knee brace 101. This can advantageously lower the level of unloading required from the unloading knee brace, allowing the knee brace to be made smaller and/or simpler than in the prior art. This can result in unloading knee braces that are less bulky, lighter-weight, and more comfortable to wear.

Unloading the affected compartment of the knee with both the lateral wedge 100 and the unloading knee brace 101 can also augment unloading of the knee. As discussed above, many known unloading knee braces provide only a limited level of unloading because of undesirable rotational forces generated by the knee brace. By unloading the affected compartment of the knee with both the lateral wedge 100 and the unloading knee brace 101, the affected area of the knee can be unloaded to a level above the functional capacity of the knee brace 101 alone. This advantageously provides greater pain reduction and increased mobility levels in the knee, improving management of the symptoms of compartmental OA of the knee.

The level of unloading provided by the lateral wedge 100 can be selected based on the level of unloading provided by the unloading knee brace 101. For instance, if a user or clinician desires to unload about 5 N m of the affected compartment of the knee and the unloading knee brace 101 unloads about 4 N m, the lateral wedge 100 can be configured so that the lateral wedge unloads about 1 N m. If the user or clinician desires to unload about 5 N m of the affected compartment of the knee and to reduce the corrective force applied to the knee by the unloading knee brace 101, the unloading knee brace 101 can be adjusted to unload about 3 N m and the lateral wedge 100 can be configured so that the lateral wedge unloads about 2 N m. In other embodiments, the lateral wedge 100 and/or unloading knee brace 101 can provide more or less unloading.

In other embodiments, the lateral wedge 100 can be used as an alternative treatment option to an unloading knee brace. This allows the user to offload the affected compartment of the knee without having to wear a visible and relatively bulky knee brace. This also allows the user to offload the affected compartment of the knee without having to apply external forces to the knee (e.g., using a knee brace), which could negatively impact and potentially further injure the knee.

The construction of the lateral wedge 100 will now be discussed in greater detail in relation to FIGS. 6-9. The lateral wedge 100 can be formed, for example, from thermoplastic elastomers (TPE) having a durometer in the range of about 30 to about 100, about 40 to about 90, or about 50 to about 70. The lateral wedge 100 can be formed by medium-weight ethylene-vinyl acetate (EVA) foam to provide light-weight support and/or cushioning without compressing over time. This can allow the lateral wedge 100 to perform consistently over a range of environmental conditions. The lateral wedge 100 can be made from compression molded EVA foam.

Another suitable material may be an EVA cork mixture that is thermomoldable. Other suitable materials may include an artificial cork, vinyl nitrile foam, polyurethane foam, rubber, silicone material, combinations thereof, or any other suitable material. The upper surface 102 can include one or more heat formable materials to shape the upper surface 102 to the bottom of the foot.

In other embodiments, different regions of the lateral wedge 100 may vary in density and/or materials. For example, the upper surface 102 may have a greater density than the lower surface 104 or the density of the lateral wedge 100 may decrease from top to bottom, increasing the useful life of the lateral wedge 100. A forefoot region 114 can include different materials than a mid-foot region 112 and/or a heel region 110. For instance, the forefoot region 114 can include more cushioning than the mid-foot region 112.

The lateral wedge 100 can comprise a single part or a plurality of parts. The lateral wedge 100 may include a plurality of layers such as two, three, four, or any other suitable number of layers. The lateral wedge 100 can comprise a single molded part.

Figure 6:
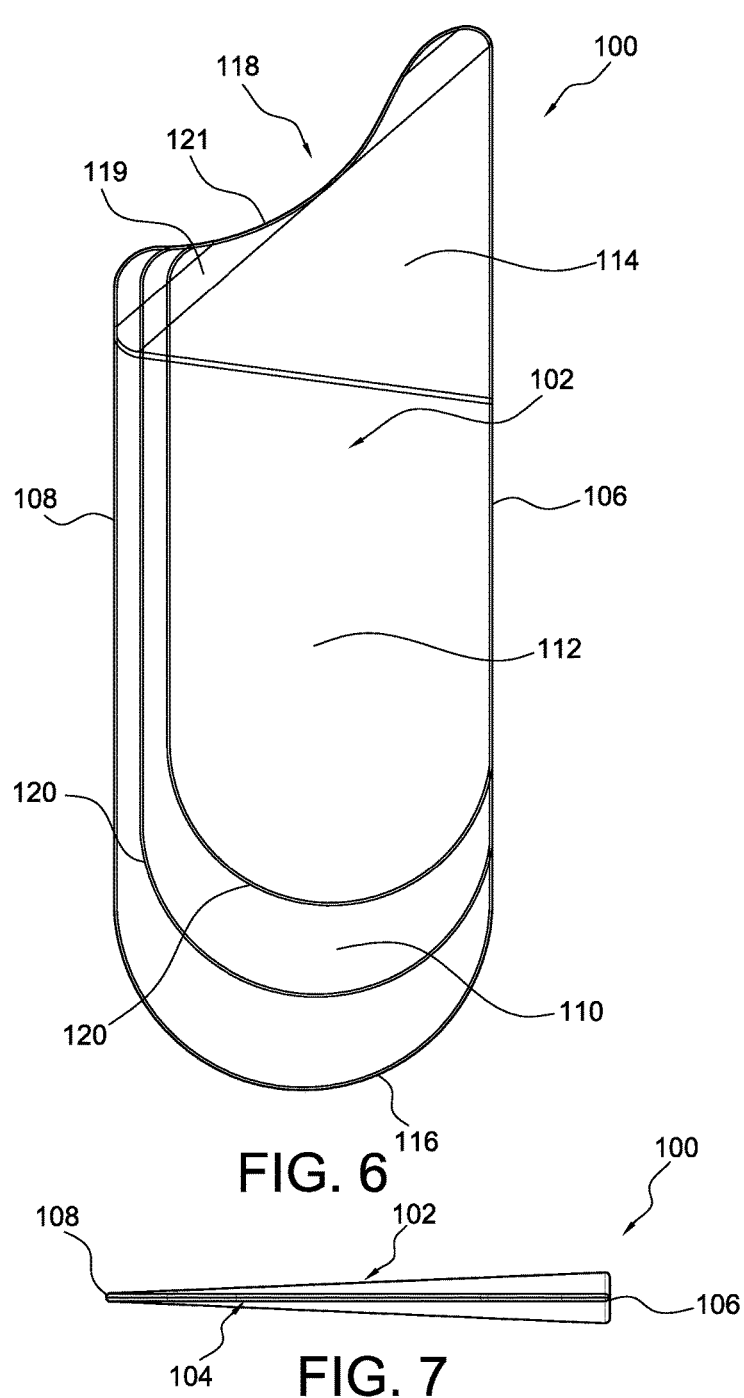
FIG. 6 a top view of the lateral wedge shown in FIG. 1.

As seen in FIG. 6, the lateral wedge 100 includes the heel region 110, the mid-foot region 112, and the forefoot region 114. The lateral wedge 100 can have an overall length less than the length of the foot. For instance, the configuration of the lateral wedge 100 can be such that when a bottom of the foot is placed on the lateral wedge 100, the heel region 110 at least in part supports the calcaneus, the mid-foot region 112 at least in part supports the navicular, cuboid and/or cuneiform bones, and the forefoot region 114 at least in part supports the metatarsus or the metatarsus and the phalanges. Alternatively, the lateral wedge 100 can have an overall length that extends generally along the entirety of the foot or a foot bed of an orthopedic device.

The lateral wedge 100 includes a posterior end in the heel region 110 having a convex shape or any other suitable shape, as indicated at 116. The lateral wedge 100 includes an anterior end 118 in the forefoot region 114. The anterior end 118 defines a cutout 121 so that when the foot is placed on the lateral wedge 100, the anterior end 118 does not extend completely below the phalanges or toes of the user. This can result in a more versatile and/or compact lateral wedge 100, allowing the lateral wedge 100 to be placed in a wider range of orthopedic devices or footwear. This can also allow at least a medial portion of the ball of the foot to rest directly on the underlying support surface, providing a connection between the foot and the support surface. Such an arrangement can help maintain the position of the foot on the lateral wedge 100.

The cutout 121 on the anterior end 118 can also vary the slope of the upper surface 102. For instance, the cutout 121 can cause the upper surface 102 near the anterior end 118 and toward the lateral side 106 of the lateral wedge 100 to have a greater slope than the upper surface 102 near the anterior end 118 and toward the medial side 108 of the lateral wedge 100. The cutout 121 can have a concave shape, an arcuate shape, an s-like shape, or any other suitable shape. Alternatively, the overall length of the lateral wedge 100 can be equal to or greater than the length of the foot. For instance, the anterior end 118 can be convex and can extend beyond the user's phalanges or toes.

Optionally, the lateral wedge 100 includes a ramped surface 119 extending diagonally between the medial side 108 and lateral side 106 and toward the cutout 121. The ramped surface 119 can be sized and configured to be positioned under the metatarsus or in any other suitable location. The ramped surface 119 extends at an angle between the upper surface 102 and the lower surface 104. The ramped surface 119 can help roll the foot of the user over along a desired line of progression (e.g., an exorotated line of progression) as the user steps forward in ambulating.

The lateral and medial sides 106, 108 extend generally between the anterior end 118 and the posterior end 116. The lateral and medial sides 106, 108 can be generally parallel or non-parallel. For instance, the width of the lateral wedge 100 between the lateral side 106 and the medial side 108 can vary, which, in turn, can vary the slope of the lateral lift provided by the lateral wedge 100.

As discussed above, the lateral wedge 100 has a thickness T decreasing from the lateral side 106 to the medial side 108 such that the upper surface 102 slopes downwardly from the lateral side 106 toward the medial side 108. The upper surface 102 can slope downward from the lateral side 106 to meet the lower surface 104 at the medial side 108 such that the medial side 108 has no vertical component or thickness T. The upper surface 102 can slope downward to the medial side 108 without meeting the lower surface 104 such that the medial side has at least some thickness T. The lateral lift provided by the lateral wedge 100 can be constant or can vary across the width of the lateral wedge 100.

Referring still to FIG. 6, the upper surface 102 of the lateral wedge 100 includes one or more trim lines 120. As used herein, the term "trim line" includes a single continuous line or a series of disconnected lines defining an area to be removed. The trim lines 120 can be arranged for reducing the size of the lateral wedge 100 to fit a particular foot, footwear, or orthopedic device. For instance, the lateral wedge 100 can be made in an extra-large size and can be trimmable to smaller sizes. The trim lines 120 can be positioned and configured for varying or controlling the lateral or medial lift of the foot. The trim lines 120 can be positioned and configured for changing the shape of the lateral wedge 100.

The lateral wedge 100 can be trimmed to a desired size and/or shape along the trim lines 120 using scissors, a razor blade, a laser, or any other suitable trimming device.

The trim lines 120 include a first portion extending across the heel region 110 and a second portion located toward the medial side 108 and extending between the first portion and the anterior end 118. The first portion of the trim lines 120 can have a convex configuration. The trim lines 120 can be on the forefoot region 114, the mid-foot region 112, the heel region 110, or on each of the forefoot region 114, the mid-foot region 112, and the heel region 110 as illustrated. The trim lines 120 can be located or formed on the upper surface 102 and/or the lower surface 104 of the lateral wedge 100. The trim lines 120 can be located or formed along the lateral side 106 or the medial side 108. The trim lines 120 can comprise a groove, a line of weakness, a marking, combinations thereof, or any other suitable feature.

It will be appreciated that the lateral wedge 100 can be configured to fit a specific size, or size range of footwear, orthopedic devices, or feet. For instance, the lateral wedge 100 can be made in extra-small, small, medium, large, and/or extra-large.

Figure 8:
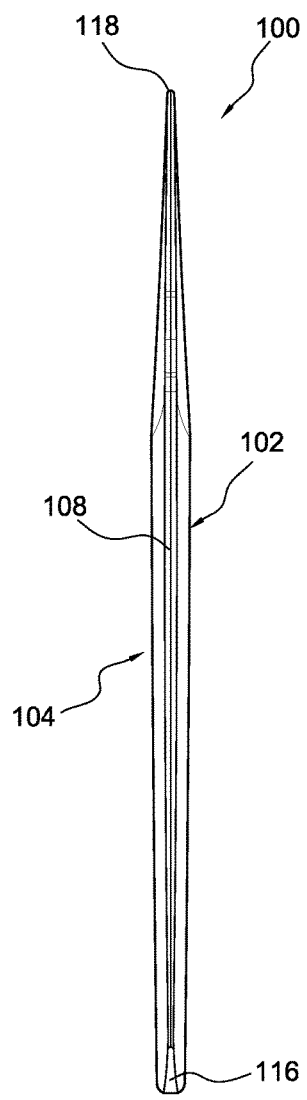
FIG. 8 is a lateral side view of the lateral wedge shown in FIG. 1.
Figure 7:
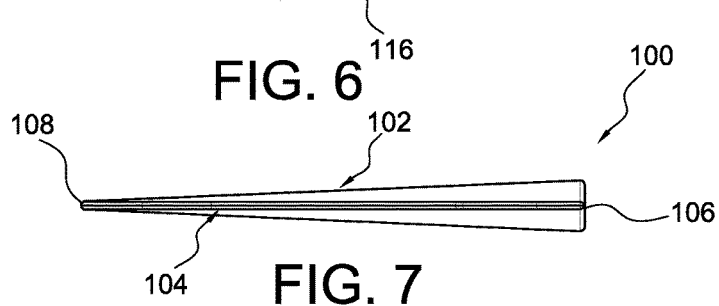
FIG. 7 a front view of the lateral wedge shown in FIG. 1.

As shown in FIG. 8, in addition to the thickness T varying between the lateral side 106 and the medial side 108 of the lateral wedge 100, the thickness T of the lateral wedge 100 can vary between the posterior end 116 and the anterior end 118 of the lateral wedge 100. This advantageously allows the lateral wedge to provide different levels of lateral lift to different portions of the user's foot. For instance, the upper surface 102 can slope downwardly or taper as it extends forward toward the anterior end 118. This can have the effect of providing more lateral lift to the heel or calcaneus of the user than the mid-foot.

The upper surface 102 can, alternatively or additionally, slope downwardly or taper as it extends back toward the posterior end 116. The contour of the upper surface 102 can be configured to increase user comfort by better fitting the natural shape of the foot. In other embodiments, the thickness of the lateral side 106 and/or the medial side 108 can be uniform, providing a generally constant lateral lift.

It should be appreciated that the lateral wedge 100 can be formed to be situated at the proper location under either a right foot or a left foot. The lateral wedge 100 can also be configured so that it can be used on the left foot or right foot. For instance, FIG. 8 illustrates the upper surface 102 and the lower surface 104 being substantially axially symmetric. As seen, the contour or slope of the lower surface 104 can be substantially the same or a mirror image of the contour of slope of the upper surface 102. This advantageously allows the same lateral wedge 100 to be used on the left or right foot by simply turning the lateral wedge 100 over. Such a configuration can allow a user to position the lateral side 106 of the lateral wedge 100 along the lateral side of the foot and to reverse the vertical position of the upper and lower surfaces (e.g., the lower surface 104 can be positioned to support the foot and the upper surface 102 can be positioned to interface with a support surface) as needed.

The lateral wedge 100 can be secured within an orthopedic device or footwear in any suitable manner. For instance, the lateral wedge 100 can be glued on top of an existing insole in an orthopedic device or footwear. The lateral wedge 100 can be glued under an existing insole in an orthopedic device or footwear. The lateral wedge 100 can be glued on the interior bottom of an orthopedic device or footwear. The lateral wedge 100 can be secured within an orthopedic device or footwear with a hook-and-loop type system on the top surface of an existing insole. The lateral wedge 100 can be integrated into the structure of the orthopedic device. For instance, the lateral wedge 100 can be integrated into the outsole of the orthopedic device.

Alternatively, the lateral wedge 100 may be held in place on top of an existing insole of the interior bottom of an orthopedic device or footwear by the weight of the user and frictional forces. The lateral wedge 100 can be secured within an orthopedic device or footwear with double-sided tape 122 as shown in FIG. 9. In an embodiment, the lateral wedge 100 can be in a left foot or right foot configuration based on whether the double-sided tape is on the upper surface 102 or the lower surface 104.

Optionally, the lateral wedge 100 includes a foot surface cover. The foot surface cover can provide cushioning. The foot surface cover can also distribute pressure over a larger area, which in turn, can limit pressure points. The foot surface cover can include any suitable material. For instance, the foot surface cover can be formed, for example, from cork, foam, fabric, combinations thereof, or any other suitable material. The foot surface cover can be made from a material that is softer than the lateral wedge 100. The foot surface cover can be soft, resilient, and can exhibit a higher coefficient of friction, which, in turn, helps prevent the foot from shifting or moving during use.

Figure 10:
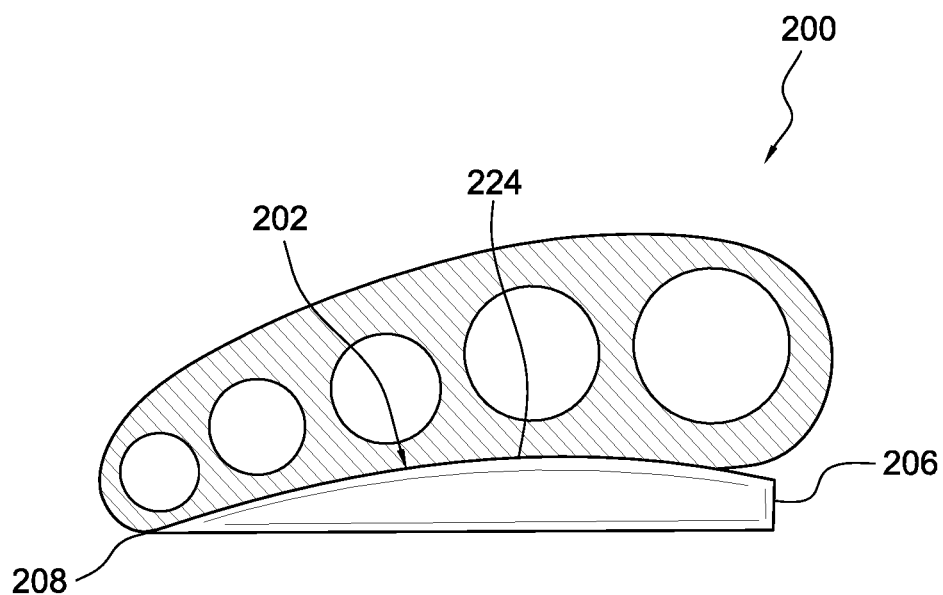
FIG. 10 is a front view of a lateral wedge according to another embodiment.

It should be appreciated that many variations of the lateral wedge having different shapes and sizes can be used for providing a lateral lift. Although such variations may differ in form, they perform substantially similar functions. For instance, FIG. 10 shows another embodiment of a lateral wedge 200 having an upper surface 202 including a convex portion 224 extending between the lateral side 206 and the medial side 208. The curvature of the convex portion 224 can increase user comfort by better fitting the transverse curve of the foot. It can also increase user comfort by reducing pressure points or pressure lines running transverse or across the plantar surface of the foot. The curvature of the convex portion 224 can also help support the user's arch. It will be appreciated that the convex portion can have other curved shapes, such as a portion of an ellipse or several arc portions.

Figure 11:
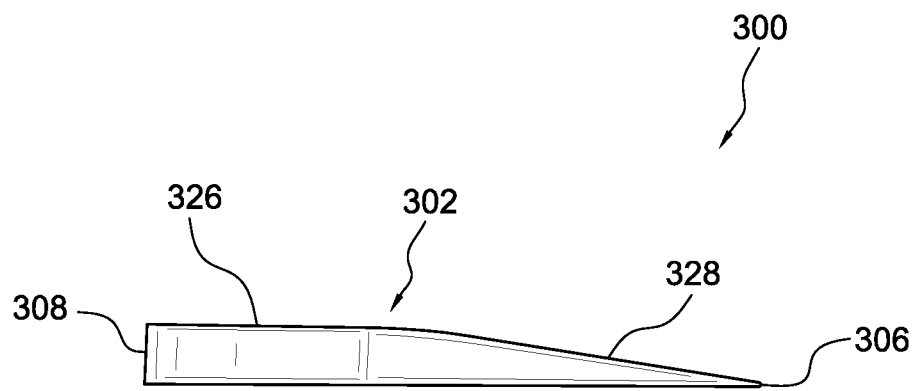
FIG. 11 is a front view of a lateral wedge according to another embodiment.

FIG. 11 shows another embodiment of a lateral wedge 300 having an upper surface 302 including a generally horizontal portion 326 extending from the medial side 308 and transitioning to an angled ramped portion 328 extending downward from the portion 326 toward the lateral side 306. The portion 326 can comfortably support the weight of the user and the ramped portion 328 can provide a lift under the medial side of the foot or medial lift. The transition between the portion 326 and the ramped portion 328 can include a radius. This can help reduce pressure points and/or lines at the transition. In other embodiments, the horizontal portion 326 can extend from the lateral side 306 and the angled portion 328 can extend downward toward the medial side 308.

Figure 12:
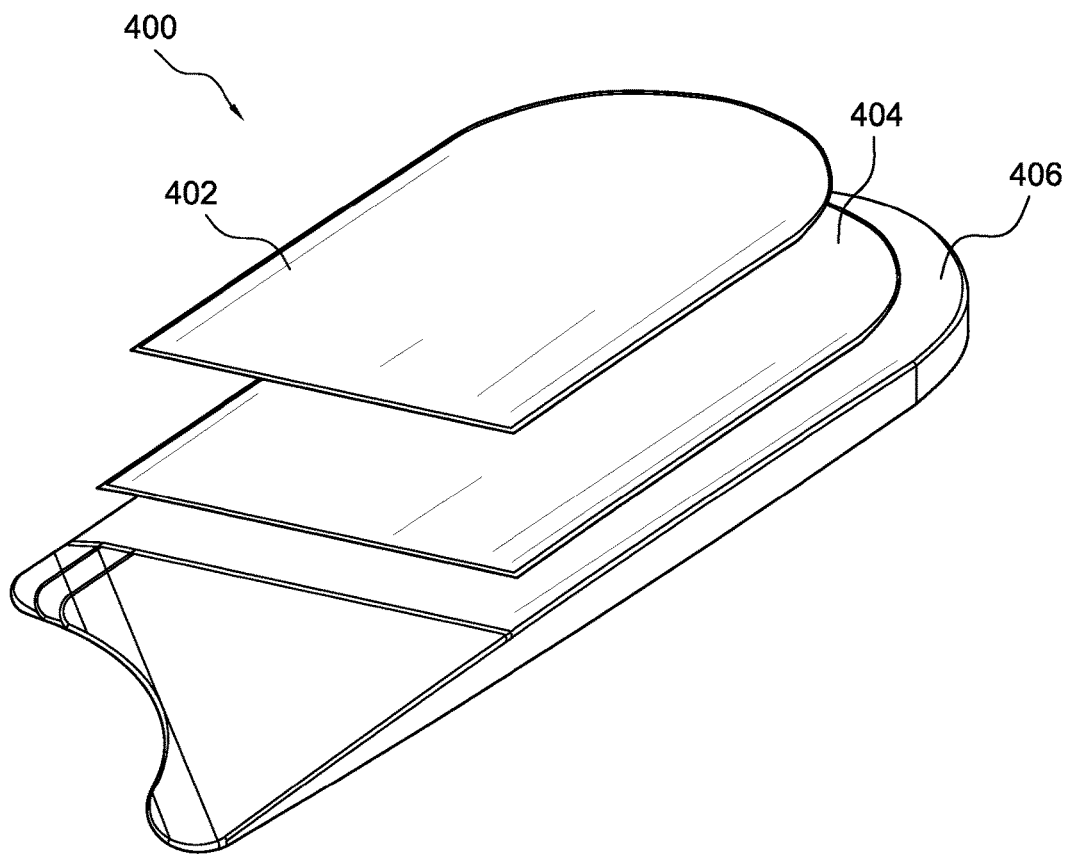
FIG. 12 is a top view of a lateral wedge according to another embodiment.

FIG. 12 shows another embodiment of a lateral wedge 400 similar to the previously described lateral wedges except that it includes a plurality of layers which can be removed to adjust the amount of lateral lift provided by the lateral wedge. As seen, the lateral wedge 400 includes a first layer 402, a second layer 404, and third layer 406. However, the number of layers shown is merely exemplary, and any suitable greater or lesser number of layers, for example 2 to 10 layers, may be used in order to achieve the desired amount and increments of lateral lift.

The layers 402, 404, 406 can be secured together with double sided tape. Alternatively, the layers 402, 404, 406 can be secured together with adhesives, hook and loop type systems, a post inserted in a corresponding hole, frictional forces, combinations thereof, or any other appropriate technique. In other embodiments, the layers 402, 404, 406 can be integrally formed and connected together at one or more parts of the lateral wedge 400. For instance, the layers 402, 404, 406 can be integrally formed with and extending from an anterior portion of the lateral wedge 400. The layer 406 can be longer and/or wider than the layer 404 and the layer 404 can be longer and/or wider than the layer 402. The layers 402, 404, 406 can have generally the same or different shapes.

In use the lateral wedge 400 can be positioned within the foot bed of the orthopedic device with all of the layers thereof retained. Thus, the amount of lateral lift provided by the lateral wedge 400 will be at a first height. In order to adjust the lateral lift, the layers 402, 404, 406 can be incrementally removed from the lateral wedge 400.

The thickness or height of the layers 402, 404, 406 correspond to the desired incremental adjustment of the lateral lift, and may be any desired thickness or height. The layers 402, 404, 406 may have the same or different heights. The layers 402, 404, 406 can have different slopes.

To adjust the lateral lift provided by the lateral wedge 400 at a first time, the lateral wedge 400 can be removed from the foot bed of the orthopedic device. Then, the third layer 406 can be removed from the lateral wedge 400, which can then be replaced in the foot bed of orthopedic device. This process can be repeated as necessary by removing layers 404 and 402 in succession. It is noted that if greater lateral lift adjustment is needed, more than one of the adjacent layers can be removed simultaneously.

The layers 402, 404, 406 can be made from any suitable material including any of the materials described above. The layers 402, 404, 406 can be formed of the same materials. The layers 402, 404, 406 can be made from different materials and/or vary in density. For instance, the layer 402 can include a heat formable material, the layer 406 can include a high density resilient material, and the layer 404 can include a compressible and resilient layer.

FIGS. 13A-13D show another embodiment of a lateral wedge 500 having one or more trim lines arranged for varying or controlling the lateral lift of the user's foot. The lateral wedge 500 includes an upper surface 502, a lower surface 504, and opposite first and second or lateral and medial sides 506, 508. A portion of the foot can rest on the upper surface 502 and the lower surface 504 can interface with a support surface. Similar to the previously described embodiments, the lateral wedge 500 includes a heel region 510, a mid-foot region 512, and a forefoot region 514. The heel region 510 has a posterior end 516 having a convex configuration and the forefoot region 514 includes an anterior end 518. A cutout 521 is defined on the anterior end 516 to that when the foot is placed on the lateral wedge 500, the lateral wedge 500 does not extend completely below the phalanges or toes of the user. Optionally, the lateral wedge 500 includes a ramped surface 519 extending diagonally between the medial side 508 and the lateral side 506 and toward the cutout 521, helping the foot to roll over along a desired line of progression.

As seen in FIG. 13B, the lateral side 506 of the lateral wedge 500 includes a thickness T1 defined between the upper and lower surfaces 502, 504. The thickness T1 tapers from the lateral side 506 toward the medial side 508 so that the upper surface 502 descends or generally slopes downwardly from the lateral side 506 toward the medial side 508. When the lateral wedge 500 is positioned underneath the foot, the lateral side of the foot is supported in an elevated position relative to the remainder of the foot, providing the lateral lift under the foot.

By controlling the thickness of the lateral side 506 relative to the medial side, the amount of lateral lift can be controlled. For example, increasing the thickness of the lateral side 506 relative to the medial side 508 increases the amount of lateral lift. Conversely, decreasing the thickness of the lateral side 506 relative to the medial side 508 decreases the amount of lateral lift.

As best shown in FIG. 13A, trim lines 520A, 520B are formed along the upper surface 502, each including a first portion 523A, 523B extending across the heel region 510 and a second portion 525A, 525B located toward the lateral side 506 and extending between the first portion 523A, 523B and the anterior end 518.

The two trim lines 520A, 520B are shown. However, the number of trim lines shown is merely exemplary, and any suitable greater or lesser number of trim lines, for example, 1 to 6 trim lines, may be used in order to achieve the desired amount and increments of lateral lift.

In use, the lateral wedge 500 in a first or untrimmed configuration can be positioned within the foot bed of the orthopedic device. Thus, the amount of lateral lift provided by the lateral wedge 500 will be at a first height generally corresponding to thickness T1 as shown in FIG. 13B.

In order to vary or control the lateral lift, the lateral wedge 500 can be trimmed along the trim lines 520A, 520B to decrease the thickness of the lateral wedge 500 along the lateral side 506. The thickness of the lateral wedge 500 along the trim lines 520A, 520B correspond to the desired adjustment of the lateral lift, and may be any desired thickness. The difference in thickness between the trim lines 520A, 520B and the lateral side 506 may be the same or different.

To adjust the lateral lift provided by the lateral wedge 500 at a first time, the lateral wedge 500 can be removed from the foot bed of the orthopedic device. Then, the lateral wedge 500 can be trimmed along the trim line 520A, reducing the thickness of the lateral wedge 500 along the lateral side 506 from T1 to Ta, which, in turn, decreases the lateral lift provided under the foot as shown in FIG. 13C. This process can be repeated as necessary by trimming the lateral wedge 500 along trim line 520B to reduce the thickness of the lateral wedge 500 along the lateral side 506 from Ta to Tb, further decreasing the lateral lift provided under the foot as shown in FIG. 13D. It is noted that if greater lateral lift adjustment is needed, the lateral wedge 500 can be trimmed along trim line 520B without first trimming the lateral wedge 500 along the trim line 520A.

A user or clinician can thus beneficially control or vary the lateral lift of the foot by trimming the lateral wedge 500 along the trim lines 520A, 520B. It will be appreciated that the degree of adjustment or control can be selected based on the construction of the lateral wedge 500, a desired treatment protocol, needs of a patient, and/or other requirements.

Figure 14:
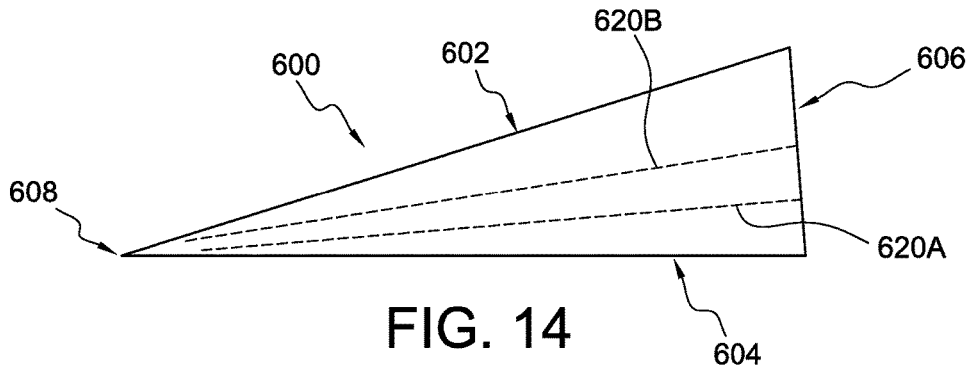
FIG. 14 is a front view of a lateral wedge according to another embodiment.

FIG. 14 shows another embodiment of a lateral wedge 600 having one or more trim lines for varying or controlling the lateral lift of the user's foot. The lateral wedge 600 includes an upper surface 602, a lower surface 604, and opposite first and second or lateral and medial sides 606, 608. The lateral wedge 600 includes a thickness that tapers from the lateral side 606 toward the medial side 608 so that the upper surface 602 descends or generally slopes downwardly from the lateral side 606. When the lateral wedge 600 is positioned underneath the foot, the lateral side of the foot is supported in an elevated position relative to the remainder of the foot, providing the lateral lift under the foot. By controlling the thickness of the lateral side 606 relative to the medial side 608, the amount of lateral lift can be controlled.

As seen, a trim line 620A extends at a first height between the lateral side 606 and the medial side 608 through the thickness of the lateral wedge 600. A trim line 620B extends at a second height generally between the lateral side 606 and the medial side 608 through the thickness of the lateral wedge 600. It will be appreciated that the trim lines 620A, 620B also extend in a direction between the anterior and posterior ends of the lateral wedge 600. The trim lines 620A, 620B can extend along the entire length or a partial length of the lateral wedge 600.

In use, the lateral wedge 600 can be positioned within the foot bed of the orthopedic device in an original or untrimmed configuration. Thus, the amount of lateral lift provided by the lateral wedge 600 will be at a first height. In order to adjust the lateral lift, the lateral wedge 600 can be trimmed along the trim lines 620A, 620B using a cutting wire or other suitable cutting device to remove one or more portions from the bottom of the lateral wedge 600.

The thickness of lateral wedge 600 between the trim lines 620A, 620B and the lower surface 604 correspond to the desired incremental adjustment of the lateral lift, and may be any desired thickness or height. The trim lines 620A, 620B may have the same or different heights. The trim lines 620A, 620B may have the same or different slopes.

To adjust the amount of lateral lift provided by the lateral wedge 600 at a first time, the lateral wedge 600 can be removed from the foot bed of the orthopedic device. The lateral wedge 600 can then be trimmed along the trim line 620A to remove a layer-like portion from the bottom of the lateral wedge 600. The lateral wedge 600 can then be replaced in the foot bed of the orthopedic device. This process can be repeated as necessary by trimming the lateral wedge 600 along the trim line 620B. If greater lateral lift adjustment is needed, the lateral wedge 600 can be trimmed along the trim line 620B before being trimmed along the trim line 620A. A user or clinician can thus beneficially control or vary the lateral lift of the foot by trimming the lateral wedge 600 along the trim lines 620A, 620B.

Figure 15A:
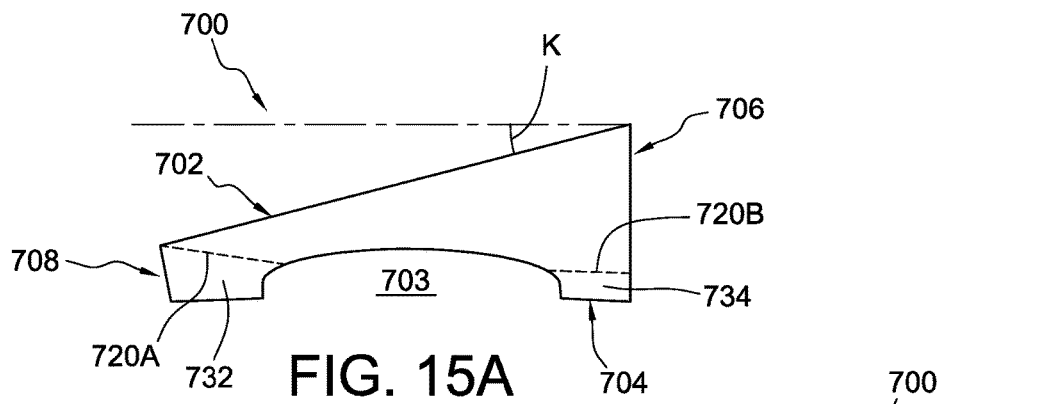
FIG. 15A is a front view of a lateral wedge according to another embodiment.
Figure 15B:
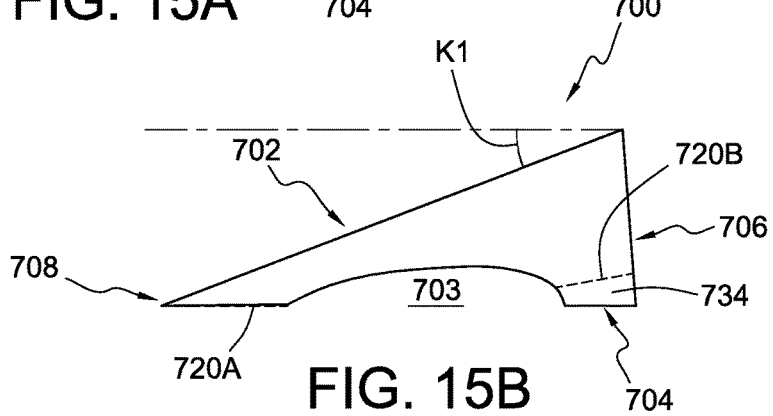
FIG. 15B is a front view of the lateral wedge of FIG. 15A trimmed along a first trim line.
Figure 15C:
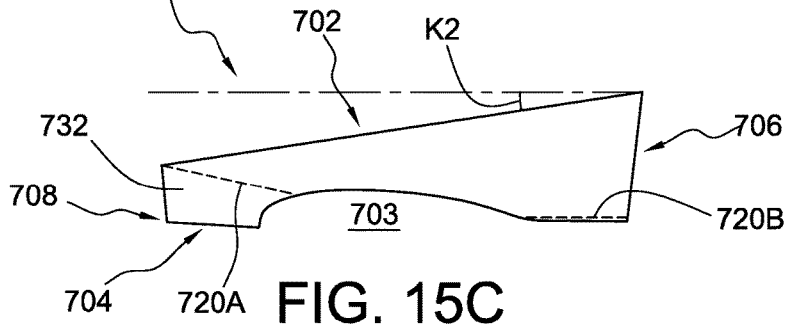
FIG. 15C is a front view of the lateral wedge of FIG. 15A trimmed along a second trim line.

FIGS. 15A-15C show another embodiment of a lateral wedge 700 having one or more trim lines arranged for varying or controlling the lateral or medial lift of the user's foot. The lateral wedge 700 includes an upper surface 702, a lower surface 704, and opposite first and second or lateral and medial sides 706, 708.

The lateral wedge 700 includes a thickness that tapers from the lateral side 706 toward the medial side 708. The upper surface 702 extends at a downward angle K relative to horizontal between the lateral side 706 and the medial side 708. The downward angle K and the thickness of the lateral side 706 relative to the medial side 708 beneficially act to provide the lateral lift under the foot. By controlling the angle K and/or the thickness of the lateral side 706, the amount of lateral lift can be controlled. For instance, increasing the downward angle K relative to horizontal can increase the amount of lateral lift. Conversely, decreasing the downward angle K relative to horizontal can decrease the amount of lateral lift.

As shown in FIG. 15A, the lower surface 704 defines a recess 703 or channel extending in a direction between an anterior end and posterior end of the lateral wedge 700. The recess 703 can have a semi-elliptical cross section, a rectangular cross section, a triangular cross section, a semicircular cross section, or any other suitable cross section. A medial support 732 is defined between the recess 703 and the medial side 708. A lateral support 734 is defined between the recess 703 and the lateral side 706. A trim line 720A extends between the recess 703 and the medial side 708 above the medial support 732. A trim line 720B extends between the recess 703 and the lateral side 706 above the lateral support 734. It will be appreciated that the trim lines 720A, 720B also extend in a direction between an anterior end and a posterior end of the lateral wedge 700. The trim lines 720A, 720B can extend along the entire length or a partial length of the lateral wedge 700.

The trim lines 720A, 720B are arranged to vary or control the lateral lift of the user's foot. For instance, trimming or cutting the lateral wedge 700 along the trim lines 720A, 720B can either increase or decrease the amount of lateral lift. In use, the lateral wedge 700 can be positioned within the foot bed of the orthopedic device in an original or untrimmed configuration. Thus, the amount of lateral lift provided by the lateral wedge 700 will be at a downward angle K as shown in FIG. 15A.

The amount of lateral lift can be adjusted by trimming the lateral wedge 700 along the trim lines 720A, 720B to remove the medial support 732 and/or the lateral support 734. To increase the lateral lift provided by the lateral wedge 700, the lateral wedge 700 can be removed from the foot bed and trimmed along the trim line 720A to remove the medial support 732 from lateral wedge 700. This drops the medial side 708 relative to the lateral side 706, creating a greater angle K1 relative to horizontal as shown in FIG. 15B.

To decrease the lateral lift provided by the lateral wedge 700, the lateral wedge 700 can be removed from the foot bed and trimmed along the trim line 720B to remove the lateral support 734 from the lateral wedge 700. This drops the lateral side 706 relative to the medial side 708, creating a lesser angle K2 relative to horizontal as shown in FIG. 15C. A user or clinician can thus beneficially increase or decrease the lateral lift of the foot by trimming the lateral wedge 700 along the trim line 720A or the trim line 720B.

While various aspects and embodiments have been disclosed herein, other aspects and embodiments are contemplated. For instance, while the lateral wedge is described in relation to the treatment of isolated compartmental OA of the knee, it will be appreciated that the lateral wedge can be used in a number of different applications, including, but not limited to, the correction and/or compensation of structural biomechanical abnormalities of the human foot and/or ankle. In order to help secure the position of the foot, in other embodiments, a separate arch support can be attachable to top surface of the lateral wedge. The arch support can be sized and configured to help maintain the position of the user's foot on the lateral wedge, preventing the foot from shifting or sliding off a side of the lateral wedge during use.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. An orthopedic system comprising:
a lateral wedge positionable under a foot of a user, the lateral wedge including:
posterior and anterior ends;
upper and lower surfaces extending between the posterior and anterior ends;
a first side extending between the upper and lower surfaces;
a second side opposed the first side;
a thickness defined between the upper and lower surfaces, wherein the thickness tapers from the first side toward the second side such that the lateral wedge is adapted to provide a lift under the foot to unload pressure from an affected compartment of the knee by supporting a lateral side of the foot or a medial side of the foot in an elevated position relative to the other;
a concave-shaped cutout defined in the anterior end and configured to terminate short of phalanges of the foot, the concave-shaped cutout extending through an entirety of the thickness of the lateral wedge and across an entirety or near entirety of a width of the lateral wedge defined between the first and second sides;
a ramped surface defined along a line running diagonally across the upper surface between the first and second sides in a forefoot region of the lateral wedge and angling downwardly from the upper surface to the concave-shaped cutout, the ramped surface configured to help direct a roll-over motion of the foot along a specific line of progression when the user steps forward on the lateral wedge; and
at least one trim line extending in a direction between the posterior and anterior ends, wherein the lateral wedge is trimmable along the at least one trim line to vary or control the amount of lift by varying the thickness of the lateral wedge along the first side relative to the thickness of the lateral wedge along the second side.

2. The system of claim 1, wherein the at least one trim line includes a plurality of trim lines formed on the upper surface toward the first side.

3. The system of claim 1, wherein the at least one trim line includes a plurality of trim lines located between the upper and lower surfaces and extending in a direction between the first and second sides.

4. The system of claim 1, wherein the lower surface defines a recess and the at least one trim line extends between the second side and the recess.

5. The system of claim 1, further comprising a knee brace adapted for positioning around a knee of the user on the same leg as the foot, the knee brace adapted to apply a first unloading to the affected compartment of the knee, and the lateral wedge adapted to apply a second unloading of the affected compartment.

6. The system of claim 5, wherein the affected compartment is the medial compartment of the knee.

7. The system of claim 1, wherein the first side comprises a lateral side of the lateral wedge, the second side comprises a medial side of the lateral wedge, and the lift comprises a lateral lift adapted to be positioned under the lateral side of the foot.

8. The system of claim 7, wherein the lateral lift varies along a length of the foot of the user.

9. The system of claim 7, wherein the lateral lift includes a first lateral lift adapted for positioning under a calcaneus of the foot and a second lateral lift under metatarsus of the foot, the first lateral lift being greater than the second lateral lift.

10. The system of claim 1, wherein the upper and lower surfaces define a same contour between the first and second sides.

11. The system of claim 1, wherein the upper and lower surfaces define a same contour between the posterior and anterior ends.

12. The orthopedic device of claim 1, wherein the upper surface defines a convex curvature between the first and second sides.

13. The system of claim 1, wherein the upper surface curves downwardly from the first side to the second side.

14. The orthopedic device of claim 1, wherein an entirety of the lateral wedge is formed from a foam.

15. An orthopedic system comprising:
a knee brace positionable around a knee of a user, the knee brace adapted to apply a first unloading of an affected compartment of the knee; and
a lateral wedge positionable under a foot of the user on the same leg as the knee brace, the lateral wedge including:
posterior and anterior ends;
upper and lower surfaces extending between the posterior and anterior ends;
a first side extending between the upper and lower surfaces;
a second side opposed the first side;
a thickness defined between the upper and lower surfaces, wherein the thickness tapers from the first side toward the second side such that the lateral wedge is arranged to apply a second unloading of the affected compartment by supporting a lateral side of the foot or a medial side of the foot in an elevated position relative to the other;
a concave-shaped cutout defined in the anterior end and configured to terminate short of phalanges of the foot, the concave-shaped cutout extending through an entirety of the thickness of the lateral wedge and across an entirety or near entirety of a width of the lateral wedge defined between the first and second sides; and
a ramped surface defined along a line extending diagonally across the upper surface between the first and second sides in a forefoot region of the lateral wedge and angling downwardly from the upper surface toward the concave-shaped cutout, the ramped surface configured to help direct a roll-over motion of the foot along a specific line of progression when the user steps forward on the lateral wedge.

16. The system of claim 15, wherein the first side comprises a lateral side of the lateral wedge, the second side comprises the medial side of the lateral wedge, and the affected compartment comprises the medial compartment of the knee.

17. The system of claim 15, wherein the first side comprises a medial side of the lateral wedge, the second side comprises the lateral side of the lateral wedge, and the affected compartment comprises the lateral compartment of the knee.

18. A method of unloading a compartment of the knee affected by osteoarthritis (OA), the method comprising:

positioning an unloading knee brace around the knee of a user to apply a first unloading of the affected compartment of the knee; and positioning a lateral wedge under a foot of the user on the same leg as the knee brace to apply a second unloading of the affected compartment of the knee, the lateral wedge including:

posterior and anterior ends;

upper and lower surfaces extending between the posterior and anterior ends;

a first side extending between the upper and lower surfaces;

a second side opposed the first side;

a thickness defined between the upper and lower surfaces, wherein the thickness tapers from the first side toward the second side such that the lateral wedge is adapted to provide a lift under the foot by supporting a lateral side of the foot or a medial side of the foot in an elevated position relative to the other;

a concave-shaped cutout defined in the anterior end and configured to terminate short of phalanges of the foot, the concave-shaped cutout extending through an entirety of the thickness of the lateral wedge and across an entirety or near entirety of a width of the lateral wedge defined between the first and second sides; and a ramped surface defined along a line running diagonally across the upper surface between the first and second sides in a forefoot region of the lateral wedge and angling downwardly from the upper surface to the concave-shaped cutout, the ramped surface configured to help direct a roll-over motion of the foot along a specific line of progression when the user steps forward on the lateral wedge.

19. The method of claim 18, wherein the lateral wedge includes a plurality of layers, and the thickness of the lateral wedge is incrementally adjustable by removing at least one of the layers from the lateral wedge.

* * * * *